United States Patent
Levine et al.

[11] Patent Number: 6,081,747
[45] Date of Patent: Jun. 27, 2000

[54] DUAL-CHAMBER IMPLANTABLE PACEMAKER HAVING NEGATIVE AV/PV HYSTERESIS AND ECTOPIC DISCRIMINATION

[75] Inventors: Paul A. Levine, Santa Clarita; Kenneth Valikai, Palos Verdes Pen., both of Calif.

[73] Assignee: Pacesetter, Inc., Sylmar, Calif.

[21] Appl. No.: 09/197,410

[22] Filed: Oct. 26, 1998

[51] Int. Cl.[7] .................................................. A61N 1/365
[52] U.S. Cl. .................................................. 607/9
[58] Field of Search .................. 607/9, 25, 14, 607/28, 18

[56] References Cited

U.S. PATENT DOCUMENTS

| | | |
|---|---|---|
| 4,422,459 | 12/1983 | Simson . |
| 4,712,555 | 12/1987 | Thornander et al. . |
| 4,788,980 | 12/1988 | Mann et al. . |
| 4,809,697 | 3/1989 | Causey et al. . |
| 4,815,469 | 3/1989 | Cohen et al. . |
| 4,940,052 | 7/1990 | Mann et al. . |
| 4,944,298 | 7/1990 | Sholder . |
| 4,944,299 | 7/1990 | Silvian . |
| 5,237,992 | 8/1993 | Poore ........................................ 607/18 |
| 5,292,341 | 3/1994 | Snell ......................................... 607/30 |
| 5,340,361 | 8/1994 | Sholder .................................... 607/24 |
| 5,417,714 | 5/1995 | Levine et al. .............................. 607/9 |
| 5,507,782 | 4/1996 | Kievel et al. .............................. 607/9 |
| 5,513,644 | 5/1996 | McClure et al. . |
| 5,741,308 | 4/1998 | Sholder ...................................... 607/9 |
| 5,814,077 | 9/1998 | Sholder et al. ............................. 607/9 |

*Primary Examiner*—Scott M. Getzow

[57] ABSTRACT

A dual-chamber implantable pacemaker is configured to operate in the DDD or DDDR mode with its AV (or PV) interval automatically set to be a small time interval less than the natural conduction time of a patient. The pacemaker shortens the AV (or PV) interval in response to a verified R-wave occurring within the AV (PV) interval, which it discriminates from an ectopic R-wave by requiring the occurrence of at least three consecutive R-waves or, alternatively, the occurrence of an R-wave having a morphology that matches the morphology of a reference R-wave stored in the pacemaker's memory. When the AV (or PV) interval is set to a value that is less than the natural conduction time, preemptive ventricular pacing.

15 Claims, 6 Drawing Sheets

DUAL-CHAMBER IMPLANTABLE PACEMAKER HAVING NEGATIVE AV/PV HYSTERESIS AND ECTOPIC DISCRIMINATION

FIELD OF THE INVENTION

The present invention relates to implantable medical devices and methods, and more particularly to an implantable pacemaker that automatically adapts its atrial-ventricular (AV) delay to a value related to the measured natural conduction time of a patient, where the measured natural conduction time is measured in a way that ignores ectopic R-waves. Such pacemaker is particularly suited for maximizing the cardiac output of patients suffering from hypertrophic obstructive cardiomyopathy.

BACKGROUND OF THE INVENTION

The heart is a pump that pumps life-sustaining blood throughout the body of the patient. A good summary of how the heart performs its function of a pump, including a brief description of the physiology of the heart, may be found in U.S. Pat. No. 5,340,361, incorporated herein by reference.

A pacemaker is an implantable medical device that monitors the activity of the heart for the occurrence of P-waves and/or R-waves, and steps in with electronically generated stimuli, when needed, to force the depolarization of the atria and/or ventricles. A pacemaker-generated stimulus that is delivered to the atrium is referred to herein as an "A-pulse". A pacemaker-generated stimulus that is delivered to the ventricle is referred to herein as a "V-pulse". Most pacemakers are configured to provide an A-pulse and/or V-pulse only if a prescribed period of time has elapsed without the occurrence of a P-wave and/or an R-wave, i.e., without the occurrence of natural heartbeats.

The prescribed period of time used by the pacemaker between contraction of the ventricle and contraction of the atrium is generally referred to as the V-A Interval or the atrial escape interval. For most dual-chamber pacemaker modes of operation, only if a P-wave does not occur during the atrial escape interval will the pacemaker step in at the conclusion of such interval and generate an A-pulse.

The prescribed period of time used by the pacemaker between contraction of the atrium and contraction of the ventricle is referred to as the A-V Interval, or sometimes it is called the "AV Delay". The pacemaker, for most dual-chamber modes of operation, generates a V-pulse only if the AV Delay elapses without the occurrence of an R-wave.

In the above-described manner, the heart is thus afforded as much time as possible to beat on its own before the electronically-generated stimuli of the pacemaker are delivered to the heart, causing it to beat at the rate set by the pacemaker.

Heretofore, most cardiac patients using a pacemaker have suffered from at least one of various cardiac conditions or diseases that affect either the ability of the SA node to maintain and sustain a satisfactory heartbeat rate (hereafter "rate problems"), or the ability of the AV node or the AV bundle to conduct a suitable stimulus to the ventricle (hereafter "conduction problems"). Advantageously, both rate problems and conduction problems lend themselves well to a pacemaker solution because the underlying cardiac muscle tissue is in place and is capable of responding to the electronically-generated stimuli produced by the pacemaker.

In recent years, it has also been recognized that standard dual-chamber pacemakers can also be effective in treating individuals who have a primary abnormality of cardiac muscle function with totally normal rhythms. This is termed a cardiomyopathy. While there are subsets of cardiomyopathy, each of which has its own specific therapeutic regimens, dual-chamber pacing with a short AV delay intentionally resulting in a disordered sequence of ventricular activation, has been very effective in alleviating symptoms of chest pain, shortness of breath and syncope in patients with hypertrophic obstructive cardiomyopathy (HOCM) that has proven to be refractory to pharmacologic therapy.

In HOCM, there is a disproportionate thickening of the intraventricular septum resulting in a dynamic outflow tract obstruction with hypercontractility of the remaining muscle. This obstruction to the ejection of blood from the ventricle causes the heart muscle to work harder increasing its metabolic demand resulting in episodes of chest pain identical to angina pectoris but without concomitant atherosclerotic obstruction of the coronary arteries, shortness of breath or dyspnea and recurrent syncope. The primary therapy for this disorder is pharmacologic; using drugs which intentionally decrease the vigor of contraction. The net effect is that the degree of obstruction is reduced, improving the overall cardiac efficiency. Until recently, the only available option when pharmacologic therapy was no longer effective was an open heart operation to surgically excise a portion of the abnormally thickened muscular septum. As this is a procedure performed infrequently by most cardiac surgeons, the operative morbidity and even mortality was higher than for most cardiac operations. In recent years, it has been recognized that a disordered sequence of ventricular activation (as might occur with the spontaneous development of an intraventricular conduction abnormality called Left Bundle Branch Block (LBBB)) can delay the electrical activation of the intraventricular septum, referred to simply as the septum, thus delaying its mechanical contraction and reducing the outflow tract obstruction. The net effect is a reduction in the major symptoms associated with HOCM. In that a similar ventricular activation sequence can be induced by pacing from the right ventricular apex, dual-chamber pacing has been successfully employed to also treat these individuals who do not have any conduction system problem that would otherwise constitute a standard indication for pacing.

In accordance with the present invention, a dual-chamber pacemaker is implanted in patients suffering from HOCM and is programmed with a sufficiently short AV or PV interval to preempt the normal conduction pattern and initiate the desired disordered sequence of ventricular activation from the location of the ventricular pacing lead. During PV or AV pacing, the pacemaker delivers a V-pulse to the ventricles at a programmed delay after the occurrence of the atrial event, which atrial event could be either the occurrence of a P wave or the delivery of an A-pulse. With delivery of a V-pulse to the tissue before natural conduction is allowed to take place, the pacemaker causes electrical depolarization and resultant muscular contraction pattern that is different from the normal pattern. This altered mechanical contraction sequence, for many HOCM patients, advantageously results in a reduction in the degree of outflow tract gradient, improving cardiac output and reducing the work of the heart. The result is a reduction in the severity and incidence of the symptoms of chest pain, dyspnea and syncope.

PV or AV pacing is only effective, however, when the V-pulse is delivered to the ventricular tissue before the occurrence of an R-wave, i.e., before the ventricular tissue depolarizes. As soon as the ventricular tissue depolarizes, it becomes refractory, and will not respond to a V-pulse, until such time as it repolarizes. It is thus necessary, if AV or PV pacing is to be used, to set the AV (or PV) interval of the pacemaker to a value that is less than the patient's normal conduction time. Heretofore, this requirement has forced the AV (or PV) interval to be set to very short values, i.e., between 80 and 120 ms or shorter, because during exercise (or other periods of physical activity or physiological stress) the patient's native conduction time may shorten significantly. Thus, in order to guarantee that the pacemaker will always pace the ventricles (i.e., in order to assure that the V-pulse is delivered to the ventricular tissue at a time when it is not refractory), the AV (or PV) interval must be set to an interval that is shorter than any native conduction interval that might exist in the given patient at any given time.

Disadvantageously, setting a very short programmed AV (or PV) interval may adversely affect cardiac output because it may force ventricular contraction well before the ventricles have had sufficient time to be filled with blood from the atrium. Thus, what is needed for patients suffering from a HOCM is a pacemaker that paces the ventricles at a time in the cardiac cycle that is always less than the natural conduction time, i.e., at a time that is prior to the occurrence of an R-wave, but that is not so much less than the natural conduction. That is, what is needed is a pacemaker that automatically sets its internally-generated AV and/or PV intervals to be just short of the patient's native conduction time, thereby assuring that the AV (or PV) interval is sufficiently long to allow the blood to physically move from the atrium to the ventricles; yet remains sufficiently short to always be less than the patient's native conduction time, thereby assuring that the V-pulse is not delivered when the ventricular tissue is refractory.

Existing systems, see, e.g., U.S. Pat. No. 5,340,361, incorporated herein by reference, respond to a single sensed R-wave by shortening the subsequent AV or PV interval by a programmable interval or delta. However, an ectopic R-wave that fails to represent true conduction, but rather a coincidental event following a paced or sensed atrial event, will result in a shortening of the AV or PV interval for the ensuing 256 cycles. The shortened interval may be physiologically inappropriate and cause hemodynamic deterioration.

When the AV and/or PV interval is shortened to a value that is just less than the native conduction time, there is also a need to regularly check the interval to determine whether it is still set at a value that is just less than the patient's native conduction time. This is because the patient's native conduction time will normally change over a period of time and may increase without detection, leaving the conduction time too short. A particular stair-step searching technique for regularly checking the AV and/or PV interval to determine if it is still less than the native conduction time is described in U.S. Pat. No. 5,334,220, which patent is incorporated herein by reference. It would also be desirable to employ other techniques or systems wherein the AV or PV interval is always maintained at an interval that bears the prescribed relationship to the patient's natural conduction time, thereby obviating the need to periodically "search" for such an optimum value.

Some additional techniques known in the art for carrying out ventricular pacing, and in particular, for verifying the complete ventricular capture results from application of a V-pulse, are shown in U.S. Pat. Nos. 5,507,782 and 5,514,163.

SUMMARY OF THE INVENTION

The present invention addresses the above and other needs by providing a dual-chamber programmable pacemaker, and method of operating such a pacemaker, that adaptively adjusts the pacemaker's AV interval to assure that the AV interval remains a fixed amount less than a measured natural conduction time while ignoring ectopic R-waves. The pacemaker is used to implement a method of treating a patient suffering from hypertrophic obstructive cardiomyopathy (HOCM) through preemptive ventricular pacing.

In a first embodiment of the invention, the pacemaker includes an atrial sense amplifier, ventricular sense amplifier, a pulse generator, and a control system. As is common with conventional dual-chamber pacemakers, the atrial sense amplifier senses P-waves in an atrial channel. The P-waves represent natural atrial activity. The ventricular sense amplifier senses R-waves in the ventricular channel. The R-waves represent natural ventricular activity. The pulse generator generates an atrial stimulation pulse (A-pulse) in the atrial channel in the absence of a sensed P-wave by the atrial sense amplifier within an atrial escape interval. The pulse generator also generates a ventricular stimulation pulse (V-pulse) in the ventricular channel in the absence of a sensed R-wave by the ventricular sense amplifier within an AV/PV interval. The control system defines the AV/PV interval and the atrial escape interval. The AV/PV interval begins upon the sensing of a P-wave or the generation of an A-pulse, whichever event occurs first in the atrial channel. The atrial escape interval begins upon the sensing of an R-wave or the generation of a V-pulse, whichever event occurs first in the ventricular channel.

Unlike conventional pacemakers, however the pacemaker provides for ventricular pacing by setting the AV/PV time interval to a value that is less than a measured conduction time interval by a prescribed amount, and takes extra precautions to assure that the measured conduction time is not tainted by the occurrence of an ectopic R-wave. A timer, which is part of the control system, periodically measures the conduction time interval using techniques that minimize the influence of ectopic R-waves on such conduction time measurement. The conduction time interval is the time period between atrial activity in the atrial channel and the sensing of an R-wave in the ventricular channel. The atrial activity includes the generation of an A-pulse or the sensing of a P-wave in the atrial channel, whichever event occurs first in a given cardiac cycle.

In a first aspect of the invention, the control system decreases the AV/PV interval by a first prescribed interval (e.g., by 20 ms) after a first prescribed number of consecutive cardiac cycles in which a sensed R-wave occurs within the AV time interval. In one embodiment, the first prescribed number of consecutive cardiac cycles in which the control system looks to find an R-wave in the AV-PV interval is preferably at least 3 cardiac cycles, however, this could be a programmable value selected by the physician. In this way, a single ectopic R-wave will not trigger a decrease to an unphysiologic AV interval and the hemodynamics of the patient will be preserved.

Secondly, the occurrence of an R-wave resulting from natural A-V conduction may be verified by monitoring the conduction time interval (e.g., for at least three, or a programmable number of, consecutive sensed R-waves) and computing an average of the conduction time interval measurements thus made. Because it is highly unlikely that three or even two consecutive ectopic R-waves would ever occur, the natural conduction time measurement is thus not likely to be tainted by ectopic R-waves if the measurement is based on the occurrence of, e.g., at least three consecutive R-waves of similar timing. The control system, after the detection of a verified R-wave, decreases the AV/PV time interval by the first prescribed interval such that the AV/PV interval of the pacemaker is set to a value that is from 5–100 ms less than the average conduction time interval.

Further, the control system may decrease the AV/PV time interval only if the natural conduction time for each R-wave of the last three consecutive sensed R-waves exceeds a predetermined conduction time range of plus or minus 25 ms of the average conduction time. Again, this helps ensure that an ectopic R-wave (which is not likely to meet this criteria) will not be considered.

In a second aspect of the invention, the control system increases the AV/PV time interval by a second prescribed interval (e.g., by 20 ms) after a second prescribed number of consecutive cardiac cycles without a sensed R-wave. This process is repeated until an R-wave occurs. Thereafter, when the first prescribed number of consecutive cardiac cycles occurs with a sensed R-wave falling within the AV time interval, then the AV/PV time interval is again decreased to a value that is less than the measured conduction time interval by the first prescribed interval.

In order to sort out ectopic R-waves, so that such ectopic R-waves do not adversely influence or taint the conduction time measurement, a more detailed feature of the present invention requires that the second prescribed number of consecutive cardiac cycles which must occur without a sensed R-wave before the control system increases the second prescribed interval comprises either a preset value (e.g., at least 3 cardiac cycles) or programmable value (e.g., between 4 and 512 cardiac cycles, corresponding to approximately 4.0 seconds and 8.5 minutes if pacing at 60 bpm). An isolated ectopic R-wave, if one occurs, would break this specified string of consecutive cardiac cycles without an R-wave. However, as repetitive, consecutive, sensed R-waves are required to define the conduction interval before the AV interval is shortened, isolated ectopic R-waves (even occurring coincidentally within the AV time interval) will not adversely affect the behavior of the pacing system.

In a second embodiment of the invention, the programmable pacemaker includes a timing circuit, a programmable processor, and sensing circuitry. The timing circuit defines a conduction time interval between a paced or sensed atrial event and a natural ventricular contraction. The programmable processor sets and derives operating parameters of the pacemaker, including an AV/PV interval defined by the timing circuit. As mentioned, the AV/PV interval is the time interval between a sensed P-wave representing natural atrial contractions or generation of an A-pulse, representing an atrial stimulation pulse, and a V-pulse representing a ventricular stimulation pulse, in absence of a sensed R-wave. The sensing circuitry electrically senses atrial and ventricular depolarizations. The processor reduces an initial value of the AV/PV interval by a predetermined time interval in response to at least three consecutive sensed R-waves, indicative of repetitive natural ventricular contractions, and returns the AV/PV interval to its initial value after a predetermined number of ventricular depolarizations.

In another similar embodiment of the present invention, the pacemaker similarly includes a sensing circuitry, a timing circuit, and a programmable processor. The sensing circuitry electrically senses P-waves and R-waves that are associated with natural atrial and ventricular contractions, respectively. The timing circuit measures a conduction time interval between a P-wave or a sensed atrial event and an R-wave or a paced ventricular event. The programmable processor sets and derives operating parameters of the pacemaker, including the AV/PV interval. The AV/PV interval is set to a value that is a prescribed time interval less than the last measured conduction time interval. Upon the sensing of an R-wave, the processor compares the sensed R-wave with a sensed R-wave stored in the processor's memory to verify that the sensed R-wave is the result of a conducted ventricular contraction and is not the result of an ectopic ventricular contraction. The processor decreases the value of the AV/PV interval by a first predetermined time interval in response to a predetermined number of consecutive verified R-waves sensed by the sensing circuitry, indicative of natural ventricular contractions.

In other more detailed features of the invention, the processor may select the reference R-wave from a plurality of R-wave morphologies stored in the processor. More particularly, the processor may select the reference R-wave under external control through a telemetry link. Alternatively, the pacemaker may further include a physiological sensor that generates a signal representing the patient's physiological condition, and the processor may automatically select the reference R-wave based on the patient's state signal.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
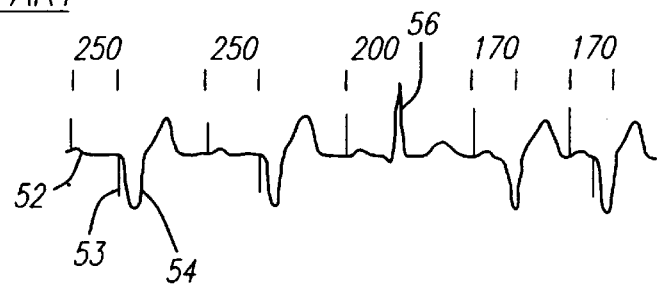
FIG. 1 is a timing diagram indicating preemptive ventricular pacing for treatment of hypertrophic obstructive (HOCM) cardiomyopathy exhibiting immediate AV/PV interval adjustment in response to a single R-wave.

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to an implantable dual-chamber pacemaker, and a method of operating an implantable dual-chamber pacemaker, that maintains its AV interval (or PV interval) at a value that is less than the heart's natural conduction time and that thereafter automatically adapts or adjusts the AV/PV interval based on the detection of, or lack of detection of, R-waves.

More specifically, if the pacemaker detects and verifies the occurrence of R-waves, indicating a shortening of the natural conduction time interval, the pacemaker shortens the AV/PV interval by a prescribed time interval. After a prescribed number of cardiac cycles without detecting an R-wave, the pacemaker lengthens the AV/PV interval by a prescribed time interval, until the AV/PV interval is at its initial value or until the next periodic measurement of the natural conduction time.

The natural conduction time is measured by the pacemaker as the time interval between an atrial event, which could either be a P-wave or an A-pulse, and an R-wave. Throughout the remaining description of the invention, unless the context indicates otherwise, the natural conduction time (whether measured from a P-wave or an A-pulse) is generically referred to as $t_{AR}$. Once the natural conduction time has been determined, the AV (or PV) interval of the pacemaker is set to a value that is a slightly less than $t_{AR}$, e.g., $t_{AR}$ minus $\Delta$, where $\Delta$ is a programmable number of from, e.g., 5–100 ms. The natural conduction time is thereafter periodically determined, e.g., every x cardiac cycles (where x is a prescribed number, e.g., from 10 to 1024) by the sensing circuits of the pacemaker, so that the AV (or PV) interval can be regularly updated to remain just less than the most-recently determined $t_{AR}$.

The pacemaker reduces the potentially deleterious effects of ectopic R-waves by several methods. One method involves requiring the occurrence of at least three consecutive A-R or P-R complexes (hereinafter simply referred to as an "R-wave") before reducing the AV/PV interval. This method is further described with reference to FIGS. 1 through 2C which show timing diagrams of cardiac cycles. Each cardiac cycle is shown commencing with a P-wave 52, representing natural atrial activity. Each P-wave is initially followed by a V-pulse 53, representing a ventricular stimulation pulse. If V-pulse 53 is of sufficient energy, it captures the ventricle and is followed by a paced R-wave 54. For purposes of the present invention, and the discussion that follows, it is assured that a V-pulse 53 always captures the ventricle, thereby causing a paced R-wave 54 to occur immediately after the V-pulse. For the sake of clarity, a paced R-wave 54 is shown as a negative-going pulse while a naturally occurring (non-paced) R-wave 56, representing natural ventricular activity, is represented by a positive-going pulse.

FIG. 1 depicts the operation of a conventional pacemaker having an adaptive AV/PV interval. See, e.g., U.S. Pat. No. 5,340,361. Such pacemaker shortens the AV/PV interval in response to only one R-wave 56. More particularly, as can be determined in FIG. 1, the AV/PV interval is initially set, based on the natural conduction time, to 250 ms and upon the occurrence of a single R-wave 56 after a conduction time interval $t_{AR}$ of only 200 ms, the AV/PV interval is shortened to 170 ms.

Figure 2A:
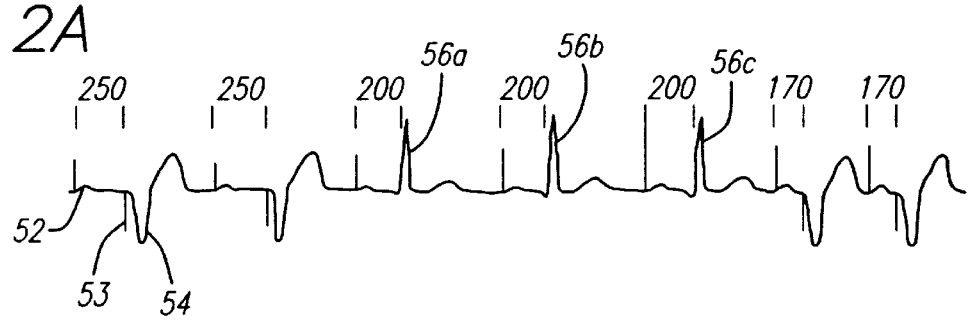
FIG. 2A is a timing diagram indicating preemptive ventricular pacing for treatment of HOCM exhibiting AV/PV interval adjustment in response to three consecutive R-waves, in accordance with the present invention.
Figure 2B:
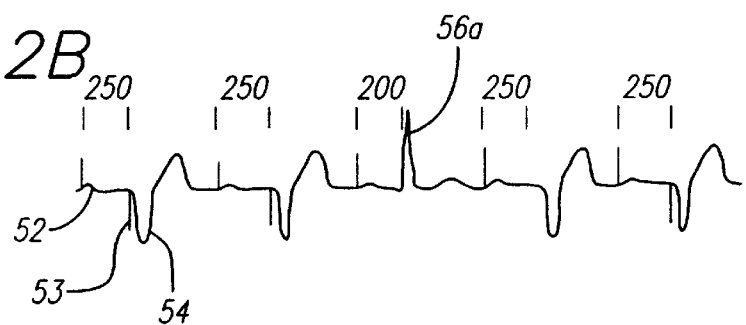
FIG. 2B is a timing diagram indicating preemptive ventricular pacing for treatment of HOCM cardiomyopathy exhibiting no AV/PV interval adjustment in response to a single R-wave, in accordance with the present invention.
Figure 2C:
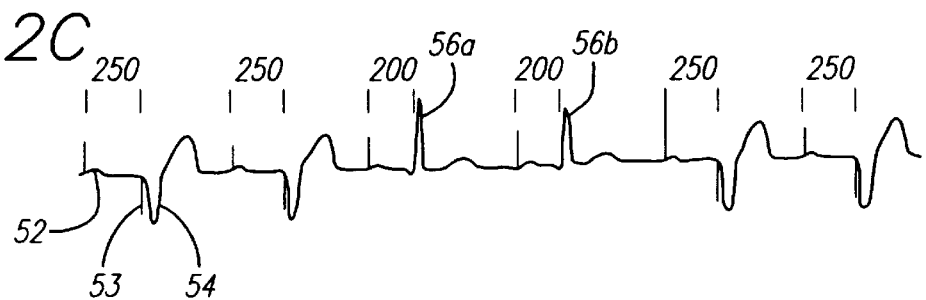
FIG. 2C is a timing diagram indicating preemptive ventricular pacing for treatment of HOCM exhibiting no AV/PV interval adjustment in response to two consecutive R-waves, in accordance with the present invention.

However, as shown in FIG. 2A, a pacemaker of the present invention shortens the AV/PV interval only after the occurrence of a prescribed number, e.g., three, consecutive R-waves 56a, 56b and 56c, each R-wave evidencing a similar conduction time interval $t_{AR}$. Thus, as seen in FIG. 2B, the single occurrence of an R-wave 56a, or as shown in FIG. 2C, the occurrence of a pair of R-waves 56a and 56b, fails to cause the pacemaker to shorten the AV/PV interval.

Figure 3A:
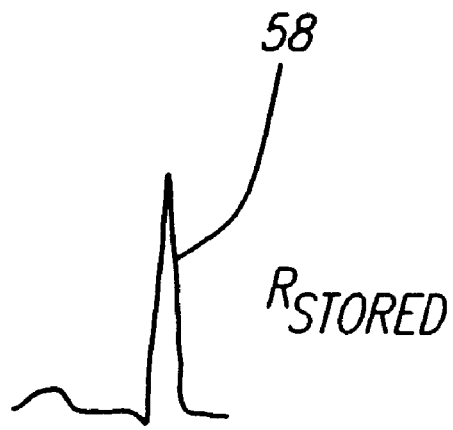
FIG. 3A is a graph showing a representative shape or morphology of an R-wave resulting from natural AV conduction.
Figure 3B:
FIG. 3B is a graph showing various representative measured natural and ectopic R-waves for morphology comparison with the standard R-wave of FIG. 3A.

Another method for reducing the tainting effects of ectopic R-waves relative to determining the natural conduction time involves analyzing the morphology of an R-wave and, based on the morphology analysis, determining whether the R-wave is an ectopic R-wave before reducing the AV/PV interval. As seen in FIG. 3A, the morphology of a naturally occurring R-wave 58 is measured and stored. Such stored R-wave is then compared against the morphology of other R-waves that occur. For example, a comparison between hypothetical R-waves, shown in FIG. 3B, and the reference R-wave 58, shown in FIG. 3A, would result in a match only for the first measured R-wave 59.

One application of the invention, and the principal application described hereinafter in more detail, is to treat patients suffering from hypertrophic obstructive cardiomyopathy (HOCM). In such instances, the AV (or PV) interval of the pacemaker is first set to a value that is less than the natural conduction time, $t_{AR}$, by a prescribed amount $\Delta$, thereby assuring that ventricular pacing (in the absence of a decreasing $t_{AR}$) will preempt a natural depolarization (R-wave). Upon the detection of non-ectopic R-waves, indicating a decreasing natural conduction time $t_{AR}$, the AV/PV interval is decreased to assure ventricular pacing. Such ventricular pacing advantageously alters the mechanical contraction sequence of the cardiac tissue so as to favorably improve the performance of the heart.

Figure 4:
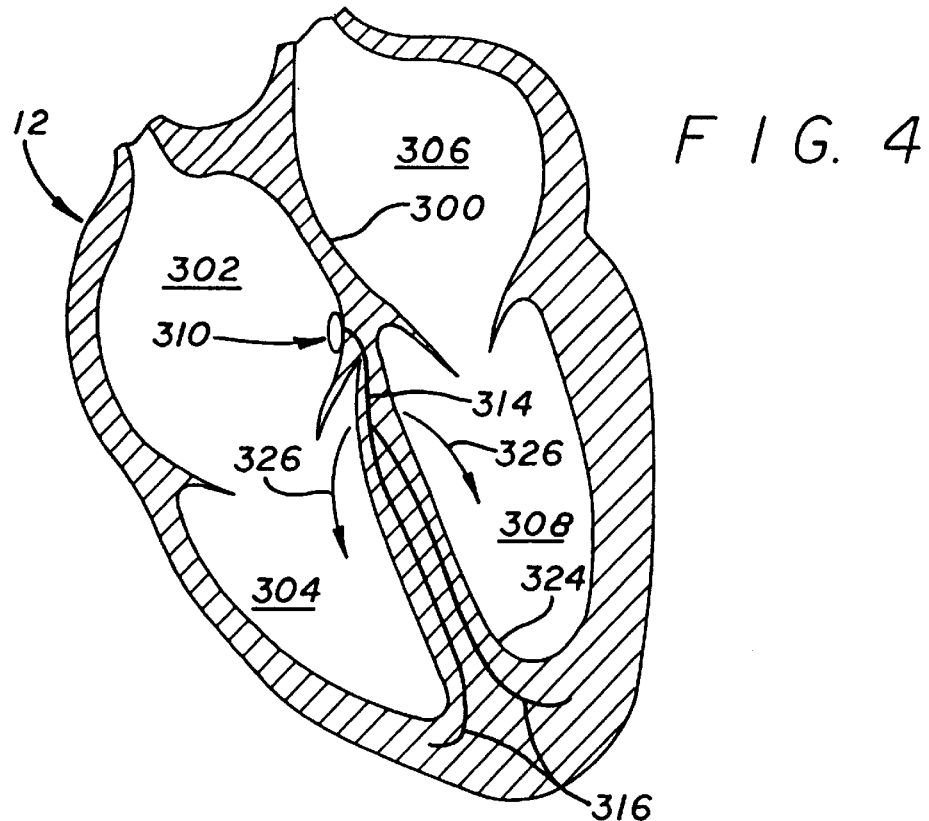
FIG. 4 is a schematic cross-sectional representation of a healthy heart.
Figure 5:
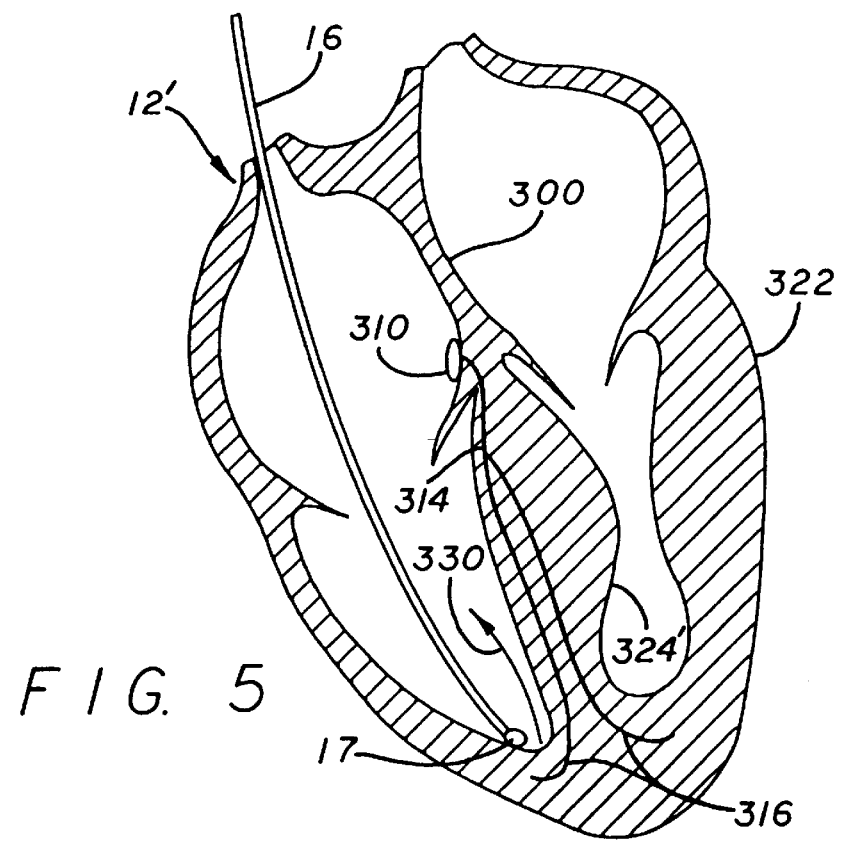
FIG. 5 is a schematic cross-sectional representation of a heart suffering from HOCM.

In order to explain the effect of a cardiomyopathy, reference is made to FIGS. 4 and 5, where there is shown a schematic cross-sectional representation of a healthy heart 12 (FIG. 4) and a heart 12' suffering from a HOCM (FIG. 5). Referring first to FIG. 4, the healthy heart 12 includes four chambers, a right atrium 302, a right ventricle 304, a left atrium 306, and a left ventricle 308. The right side of the heart is separated from the left side of the heart by a wall of tissue, or septum 300 and 324. The AV node 310 is located in the intra-atrial septum 300. A bundle of His 316 also lies in the intra-atrial septum 300, and provides a path through which a suitable stimulus is carried from the AV node 316 to the ventricular tissue near the apex of the heart. In response to such a stimulus, the ventricular tissue begins to contract, commencing along the intra-ventricular septum 324 in the direction of the arrows 326. Such contraction triggers a particular type of mechanical or physical action within the heart that forces the blood held in the ventricles out appropriate arteries (not shown) to desired body tissue locations.

In FIG. 5, there is shown a schematic representation of a heart 12' that suffers from hypertrophic obstructive cardiomyopathy. The left ventricular muscle mass 322, is even thicker than the muscle of the normal heart with the intra-ventricular septum 324' being the thickest of all causing it to bulge into the left ventricular cavity. With normal electrical conduction, the intra-ventricular septum 324' further thickens and acts like a splint with the rest of the ventricle bending around this structure. Effectively, this causes a relative or dynamic obstruction to the ejection of blood into the aorta. By artificially inducing a disordered sequence of activation, the vigor of contraction is reduced decreasing the degree of obstruction and improving cardiac function.

The improvement in the cardiac output is caused, at least in part, by the fact that the stimulated contraction of the heart 12' starts at a different location (i.e., at or near the electrode tip 17 of a ventricular pacing lead 16), than does a natural apical contraction. The resulting stimulated contraction is represented in FIG. 5 by the arrow 330. Such stimulated contraction advantageously produces a different mechanical or physical sequence of the ventricular contraction than is achieved through a natural apical contraction 44 (FIG. 4). Such different mechanical sequence, in turn, creates pumping forces within the contracting muscle tissue that enhances the cardiac output. Further, for some patients, a continued treatment using preemptive ventricular pacing as described herein results in a marked improvement in cardiac output over time. That is, the continued application of a ventricular stimulus so as to cause a different mechanical contraction sequence appears to cause a thinning of the thick cardiomyopic walls of the heart, and a strengthening of the ventricular muscle tissue, thereby effecting not only a treatment for a cardiomyopathy, but also a cure.

To this end, the present invention determines the natural conduction time between a P-wave (evidencing depolarization of the atria) and a subsequent R-wave, or P-R interval, and sets the PV interval of the pacemaker to be a prescribed amount less than such P-R interval. Alternatively, should the atria of the patient also require stimulation, the invention determines the paced conduction time between an atrial stimulation pulse, (A-pulse) and a subsequent R-wave, or A-R interval, and sets the AV interval of the pacemaker to be a prescribed amount less than such A-R interval. In this manner, the pacemaker always delivers a V-pulse at the conclusion of the PV or AV intervals, which (for treating HOCM) is less than the natural conduction time (P-R or A-R interval), and hence before the ventricles attempt to contract on their own. In determining the A-R interval, any of the techniques described above for distinguishing between an ectopic R-wave and a natural non-paced R-wave may be used.

Advantageously, the present invention may be implemented using a wide variety of dual-chamber pacemaker configurations and pacemaker hardware. Any pacemaker configuration that allows the pacemaker to determine the natural conduction time interval, i.e., the A-R interval, untainted by ectopic R-waves, and which further allows the AV or PV intervals to be automatically set to a value that is a prescribed amount less than the A-R or P-R conduction-time intervals, may be used to implement the invention. The description that follows is only exemplary of one such configuration.

A Representative Microprocessor-Based Pacemaker

To better understand how the present invention may be practiced, it will be helpful to review the main components, and basic operation, of a pacing system. Accordingly, the following overview of a pacemaker is presented.

Figure 6:
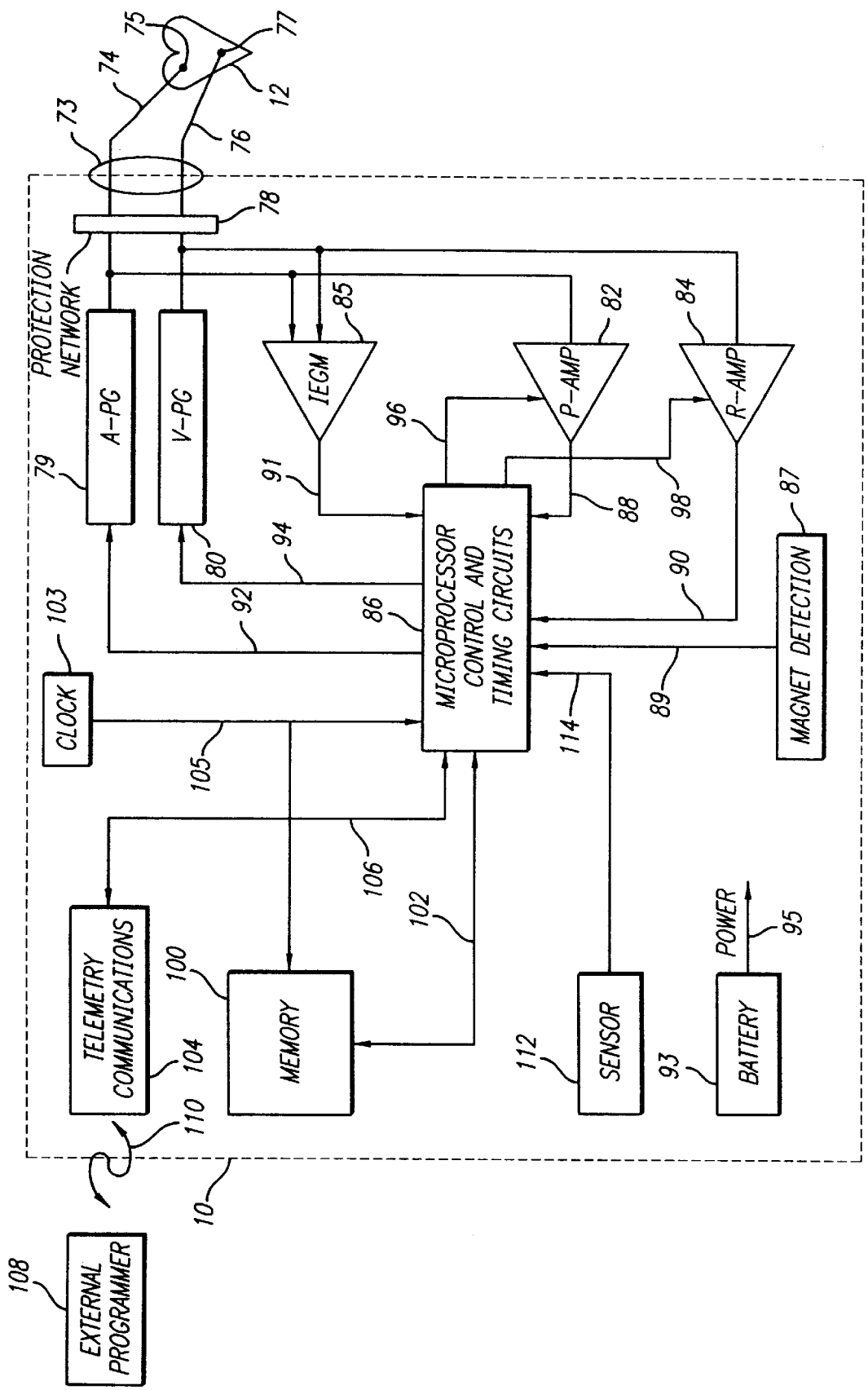
FIG. 6 is a functional block diagram of a representative multi-mode microprocessor-based implantable pacemaker that may be used with the present invention.

In FIG. 6, a functional block diagram of a dual-chamber pacemaker 10 of a type with which the present invention may be used is shown. The pacemaker 10 is coupled to a heart 12 by way of leads 74 and 76, the lead 74 having an electrode 75 that is in contact with one of the atria of the heart, and the lead 76 having an electrode 77 that is in contact with one of the ventricles of the heart. The leads 74 and 76 are electrically and physically connected to the pacemaker 10 through a connector 73 that forms an integral part of the housing wherein the circuits of the pacemaker are housed.

The connector 73 is electrically connected to a protection network 78, which network 78 electrically protects the circuits within the pacemaker 10 from excessive shocks or voltages that could appear on the electrodes 75 and/or 77 in the event such electrodes were to come in contact with a high voltage signal, e.g., from a defibrillator shock.

The leads 74 and 76 carry stimulating pulses to the electrodes 75 and 77 from an atrial pulse generator (A-PG) 79 and a ventricular pulse generator (V-PG) 80, respectively. Further, electrical signals from the atria are carried from the electrode 75, through the lead 74, to the input terminal of an atrial channel sense amplifier (P-AMP) 82; and electrical signals from the ventricles are carried from the electrode 77, through the lead 76, to the input terminal of a ventricular channel sense amplifier (R-AMP) 84. Similarly, electrical signals from both the atria and ventricles are applied to the inputs of an IEGM (intracardiac electrogram) amplifier 85. The amplifier 85 is typically configured to detect an evoked response from the heart 12 in response to an applied stimulus, thereby aiding in the detection of capture. (Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.)

The dual-chamber pacemaker 10 is controlled by a control system 86 that typically includes a microprocessor programmed to carry out control and timing functions. The control system 86 receives the output signals from the atrial (P-AMP) amplifier 82 over signal line 88. Similarly, the control system 86 receives the output signals from the ventricular (R-AMP) amplifier 84 over signal line 90, and the output signals from the IEGM amplifier 85 over signal line 91. These output signals are generated each time that a P-wave, an R-wave, or an evoked response is sensed within the heart 28. The control system 86 also generates trigger signals that are sent to the atrial pulse generator (A-PG) 79 and the ventricular pulse generator (V-PG) 80 over signal lines 92 and 94, respectively. These trigger signals are generated each time that a stimulation pulse is to be generated by the respective pulse generator 79 or 80. The atrial trigger signal is referred to simply as the "A-trigger", and the ventricular trigger signal is referred to as the "V-trigger". During the time that either an A-pulse or V-pulse is being delivered to the heart, the corresponding amplifier, P-AMP 82 and/or R-AMP 84, is typically disabled by way of a blanking signal presented to these amplifiers from the control system over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 6, the pacer 10 also includes a memory circuit 100 coupled to the control system 86 over a suitable data/address bus 102. This memory circuit 100 allows certain control parameters, used by the control system 86 in controlling the operation of the pacemaker, to be programmably stored and modified, as required, in order to customize the pacer's operation to suit the needs of a particular patient. Further, data sensed during the operation of the pacer may be stored in the memory 100 for later retrieval and analysis.

The memory 100 of the pacemaker 10 may take many forms, and may be subdivided into as many different memory blocks or sections (addresses) as needed in order to allow desired data and control information to be stored. A feature of the present invention is the ability to store a relatively large amount of sensed data as a data record, which data record may then be used to guide the operation of the device, e.g., whether a given R-wave is an ectopic R-wave or a naturally occurring R-wave. Other parameters, of course, in addition to (or in lieu of) R-wave morphology data or conduction time data, may be similarly sensed, stored, averaged (or otherwise processed), and then used for comparison purposes. Advantageously, modern memory devices allow for the storage of large amounts of data in this manner.

A clock circuit 103 directs an appropriate clock signal(s) to the control system 86, as well as to any other needed circuits throughout the pacemaker 10 (e.g., to the memory 100) by way of clock bus 105.

A telemetry/communications circuit 104 is further included in the pacer 10. This telemetry circuit 104 is connected to the control system 86 by way of a suitable command/data bus 106. In turn, the telemetry circuit 104, which is included within the implantable pacer 10, may be selectively coupled to an external programming device 108 by means of an appropriate communication link 110, which communication link 110 may be any suitable electromagnetic link, such as an RF (radio frequency) channel, a magnetic link, an inductive link, an optical link, and the like. Advantageously, through the external programmer 108 and the communication link 110, desired commands may be sent to the control system 86. Similarly, through this communication link 110 and the programmer 108, data (either held within the control system 86, as in a data latch or stored within the memory 100) may be remotely received from the pacer 10. In this manner, noninvasive communications can be established with the implanted pacer 10 from a remote, non-implanted, location.

The pacer 10 additionally includes a battery 93, which provides operating power to all of the circuits of the pacer 10 via a POWER signal line 95. The voltage of the pacemaker battery 93 on the POWER signal line 95 is monitored by appropriate monitoring circuits within the control system 86, or elsewhere within the pacemaker 10, in order to ascertain whether the battery voltage has dropped below a predefined recommended replacement time (RRT) threshold.

It is noted that the pacer 10 in FIG. 6 is referred to as a dual-chamber pacemaker because it interfaces with both the atria and the ventricles of the heart. Those portions of the pacer 10 that interface with the atria, e.g., the lead 74, the P-wave sense amplifier 82, the A-PG 78, and corresponding portions of the control system 86, are commonly referred to as the "atrial channel". Similarly, those portions of the pacer 10 that interface with the ventricles, e.g., the lead 76, the R-wave sense amplifier 84, the V-pulse generator 80, and corresponding portions of the control system 86, are commonly referred to as the "ventricular channel".

As needed for rate-responsive applications, the pacemaker 10 further includes at least one sensor 112 that is connected to the control system 86 of the pacer 10 over a suitable connection line 114. While this sensor 112 is illustrated in FIG. 6 as being included within the pacer 10, it is to be understood that the sensor may also be external to the pacer 10, yet still be implanted within or carried by the patient. Two common types of sensors include an activity sensor, such as a piezoelectric crystal, that is mounted to the case of the pacemaker and an accelerometer mounted on the circuit substrate. Other types of sensors are also known, such as sensors that sense the oxygen content of blood, respiration rate, pH of blood, body motion, and the like. The type of sensor used is not critical to the present invention. Any sensor capable of sensing a parameter relatable to the rate at which the heart should be beating can be used. Such sensors are used with "rate-responsive" pacemakers in order to adjust the basic rate (pacing cycle) of the pacer in a manner that tracks the physiological needs of the patient. To this end, the control system 86 (when operating in a rate-responsive mode) receives output signals from the sensor 112 and converts them to a sensor-indicated-rate (SIR) signal which is used by the control system 86 to set the pacing interval of the pacemaker.

The pacemaker 10 further includes magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker 10, and/or to signal the control system 86 that an external programmer 108 is in place to receive data from, or send data to, the pacemaker memory 100 or control system 86 through the telemetry communications circuits 104.

The telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art.

The control system 86 may be realized using a variety of different techniques and/or circuits. The preferred type of control system 86 is a microprocessor-based control system, as described, e.g., in FIGS. 6–8 and accompanying text of U.S. Pat. No. 5,476,487, incorporated herein by reference. It is noted, however, that the control system 86 could also be realized using a state machine. Indeed, any type of control circuit or system could be employed for the control system 86. Those of skill in the implantable medical device art, given the teachings presented herein, should thus be able to fashion numerous different types of control systems or circuits that achieve the desired stimulus pulses.

A representative alternative type of control system that could be used with the invention, for example, is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are all incorporated herein by reference.

Additional details relative to a particular multi-mode, microprocessor-based, pacemaker that may be utilized in order to implement the present invention are found in the previously-referenced U.S. Pat. No. 5,476,487. As indicated above, however, the present invention is not limited by a particular pacemaker design, but may be implemented using any pacemaker design wherein operating parameters of the pacemaker and/or the patient/pacemaker interface may be monitored, measured, and stored, and wherein the timing of ventricular stimuli may be implemented in the manner described herein.

Figure 7:
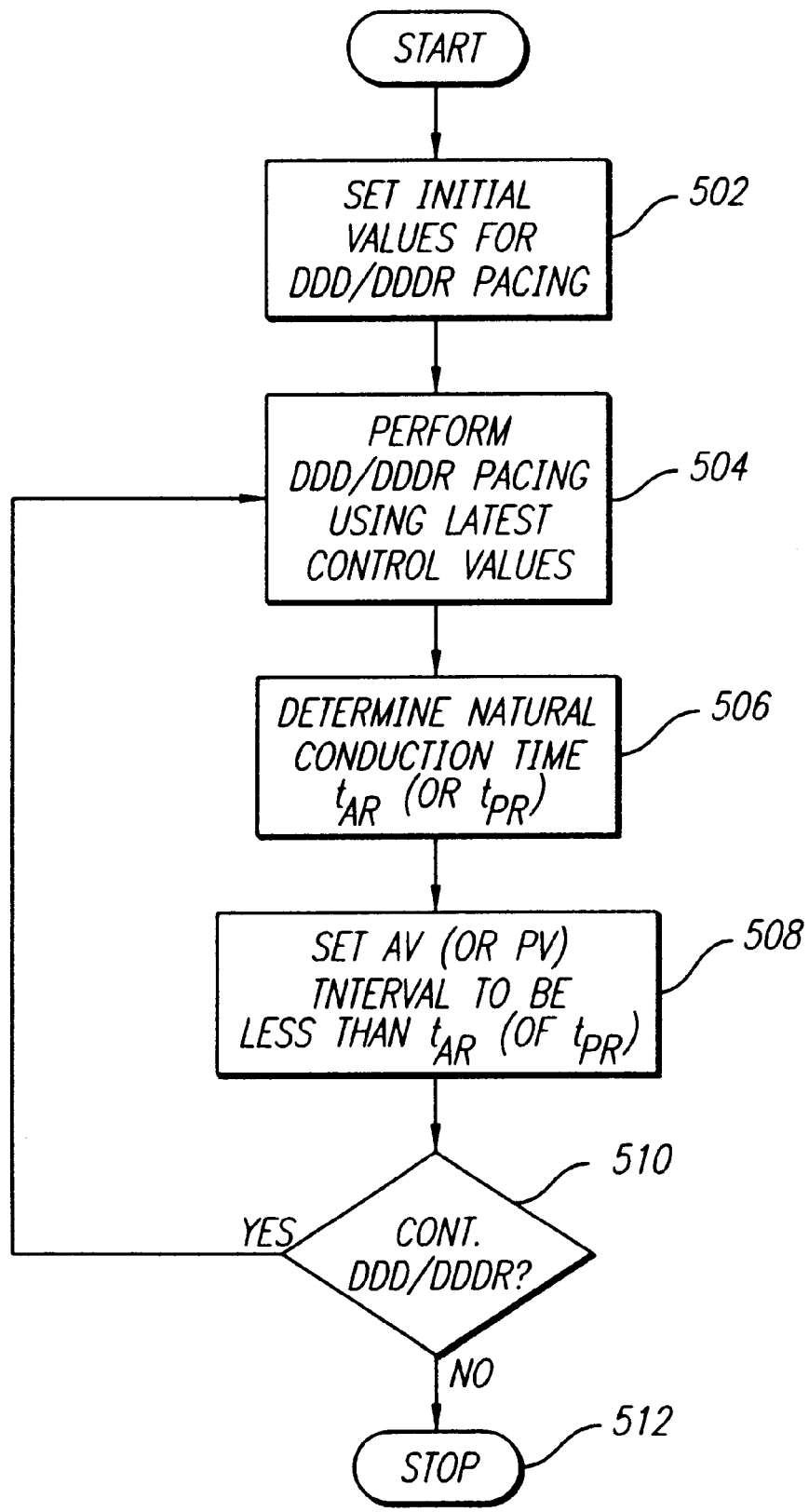
FIG. 7 is a flowchart illustrating a method including the present invention.
Figure 8:
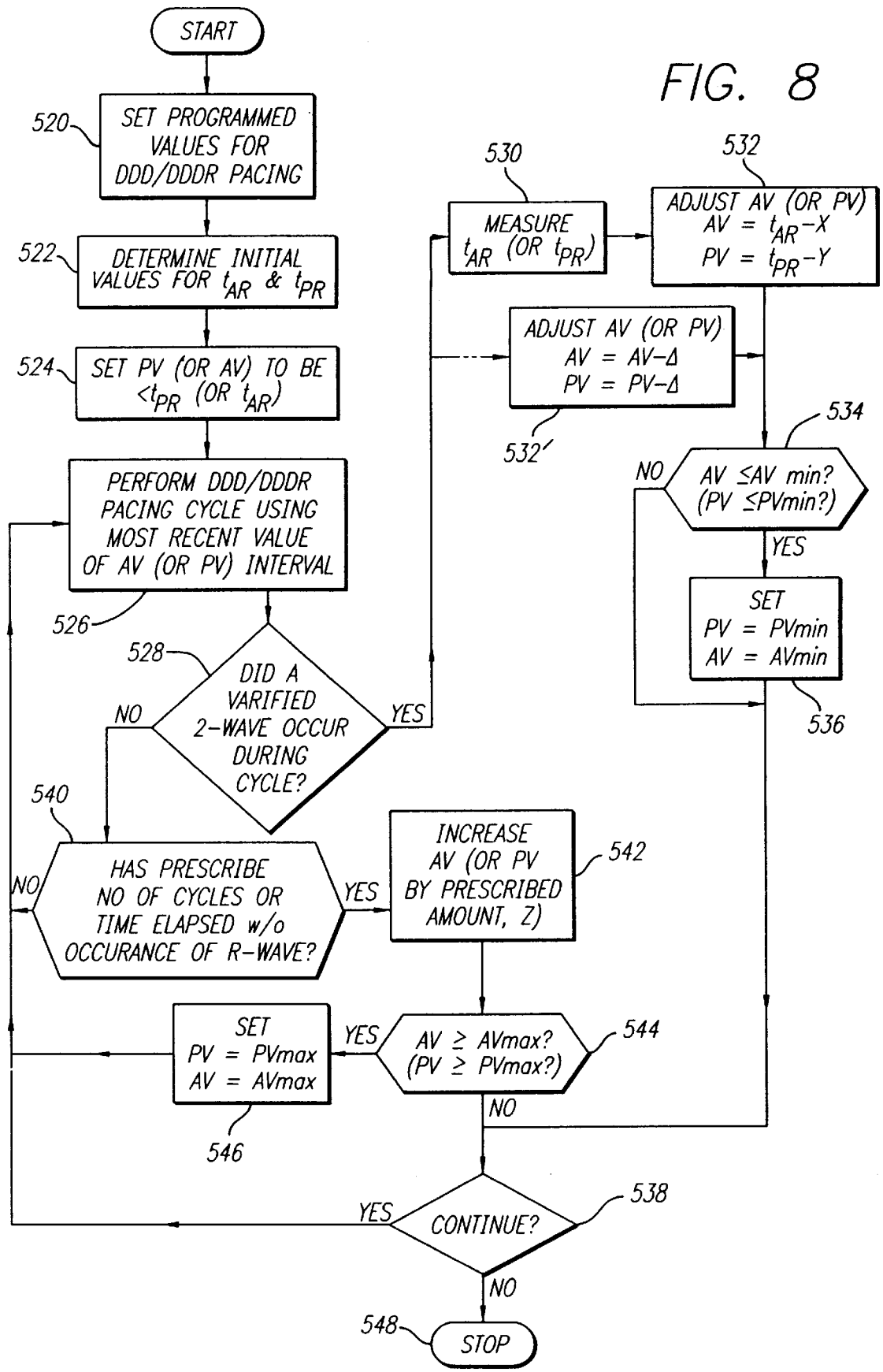
FIG. 8 is a more detailed flowchart illustrating the method of the present invention when used to provide preemptive ventricular pacing to treat HOCM.

Of primary significance to the present invention is the manner in which the AV interval (or PV interval) is adaptively adjusted to a value related to the measured natural conduction time of the patient. The manner in which this is done is illustrated in the flowcharts of FIGS. 7 and 8. FIG. 7 illustrates the operation of the pacemaker in absence of an R-wave verified to be produced by natural AV conduction; that is, a series of a predetermined or programmable number of consecutive R-waves (e.g., preferably three or more) or at least one R-wave of appropriate morphology. FIG. 8 illustrates the operation of the pacemaker in the presence of R-waves produced by natural AV conduction.

As seen in FIG. 7, the method starts by setting the initial values needed by the pacemaker to carry out, e.g., DDD or DDDR pacing (block 502). (DDD and other pacing modes are described in U.S. Pat. No. 5,237,992, which patent is incorporated herein by reference.) Such values are, for the most part, no different than those used when performing conventional DDD or DDDR pacing, and include such values as an initial pacing rate (from which an appropriate atrial escape interval is determined), an initial value for the AV interval, blanking period values, maximum pacing rate values, stimulation pulse amplitudes and widths, and the like. In accordance with the present invention, such initial values also include a minimum and maximum value for the AV (or PV) interval, plus a prescribed time difference between the natural conduction time of the patient and the pacemaker-defined AV (or PV) interval. In some embodiments of the invention, it may also be important to specify the difference between the A-R interval and a P-R interval, where the A-R interval is the natural conduction time as measured from the delivery of an A-pulse to the subsequent occurrence of an R-wave, and the P-R interval is the natural conduction time as measured from the occurrence of a P-wave to the subsequent occurrence of an R-wave.

Once the initial values needed to carry out DDD or DDDR pacing have been set, the specified DDD or DDDR pacing is carried out (block 504) in conventional manner, one cardiac cycle at a time, using the programmed values. At some point in a cardiac cycle associated with such DDD or DDDR pacing, an R-wave resulting from natural AV conduction will occur; an ectopic R-wave may occur; or a number of consecutive cardiac cycles will go by without the occurrence of an R-wave.

The occurrence of R-waves may indicate the depolarization of the ventricles as a result of a natural or native conduction time shorter than the presently existing AV (or PV) interval of the pacemaker, or the R-wave may be a single ectopic R-wave. When preemptive ventricular pacing is desired, (i.e., when treating HOCM), R-waves resulting from natural AV conduction may indicate that the pacemaker-defined AV (or PV) interval needs to be decreased.

To prevent an isolated R-wave or ectopic beat from prematurely shortening the AV interval, the control system will not determine a new natural conduction time (block 506) until a specified criteria is met, preferably, a predetermined (or programmable) number of consecutive cardiac cycles must occur without an R-wave, thereby indicating a true lengthening of the natural conduction time. Alternately, other criteria could simply include the passage of a prescribed number of cardiac cycles (e.g., between 8 and 2048), or the mere passage of time (e.g., once every 10–15 minutes) may be used to signal a need to determine the natural conduction time of the patient (block 506). In another embodiment, the R-wave must have a predetermined (or pre-characterized) morphology to distinguish true conducted R-waves from ectopic R-waves.

Accordingly, as soon as an appropriate criteria is met, then the natural conduction time, $t_{AR}$, is determined or remeasured (block 506).

The natural conduction time is determined as the time interval between the most recent atrial activity, which would be either a P-wave or an A-pulse, and an R-wave. That is, the native or natural (note, as used herein, "native" and "natural" are used as synonyms) begins with the occurrence of atrial activity, and ends with the occurrence of an R-wave. If the most recent atrial activity was a P-wave, then the conduction time measured is $t_{PR}$. If the most recent atrial activity was an A-pulse, then the conduction time measured is $t_{AR}$. (Note, heretofore $t_{AR}$ has been used to refer generically to the natural conduction time, whether technically $t_{PR}$ or $t_{AR}$).

In order to assure that the determination of $t_{AR}$ or $t_{PR}$ accurately reflects the true natural conduction time (and not tainted by an ectopic R-wave), the natural conduction time over several cardiac cycles may be measured, and then an average, mean, or other appropriate combination, of $t_{AR}$ or $t_{PR}$ over the prescribed number of cycles can be computed.

If an R-wave fails to occur for a prescribed number of cardiac cycles, then that provides an indication that perhaps the natural conduction time has increased, and that there is a need to increase the AV (or PV) interval so that it is not too different than the natural conduction time.

Once such need is identified, an appropriate adjustment to the AV (or PV) interval of the pacemaker can be made, as required (block 508). That is, once a determination is made that the natural conduction time has either decreased or increased (block 506), the AV (or PV) interval of the pacemaker is then set to a value that is just less than the determined natural conduction time. This is done by setting the AV (or PV) interval to be equal to the most recent $t_{AR}$ (or $t_{PR}$) determination minus Δ, where Δ is a programmable value, typically ranging from 5–100 ms. For example, when the pacemaker is used to treat HOCM, and when it appears that the natural conduction time has decreased (as is most often the case when an R-wave has been sensed), then the AV (or PV) interval is set to $t_{AR}$ (or $t_{PR}$) minus Δ.

After the AV (or PV) intervals have been set to be less than the determined conduction time $t_{AR}$ (or $t_{PR}$) at block 508, then a determination is made as to whether DDD or DDDR pacing is to continue (block 510). If not, then the method terminates (block 512). If so, then the method continues (block 504) by performing the DDD or DDDR pacing for the next cardiac cycle using the adjusted values of the AV (or PV) interval.

In FIG. 8, a more detailed flowchart is illustrated that shows one technique for determining or measuring the natural conduction time of the patient (block 506 in FIG. 7), and adjusting the AV (or PV) intervals accordingly (block 508 in FIG. 7). It is noted that the method shown in FIG. 7, as well as the method shown in FIG. 8, are directed primarily to using the pacemaker to treat HOCM (i.e., are directed to a method that provides preemptive ventricular pacing). However, such methods may be readily adapted by those of skill in the art for other applications of the invention.

In FIG. 8, the programmed values needed to carry out DDD or DDDR pacing are programmed into the pacemaker in conventional manner (block 520). In accordance with the present invention, such programmed values include the number of cardiac cycles that must occur without an R-wave before the AV (or PV) interval is increased, the amount of such increase, an initial value for the natural conduction time $t_{AR}$ (or $t_{PR}$), or an indication of a technique for determining such initial values, the difference X and/or Y between the natural conduction times and the AV (or PV) intervals, and the like (block 522). Once the initial values of $t_{AR}$ or ($t_{PR}$) have been determined, then the value of the AV (or PV)

interval is set to be a specified amount (e.g., Δ) less than $t_{AR}$ or $t_{PR}$ (block 524).

With the AV (or PV) interval set to an initial value, the DDD or DDDR pacing cycle commences using such value, plus the other programmed values (block 526). If an R-wave is sensed during the pacing cycle (block 528), then that may signal that the natural conduction time $t_{AR}$ (or $t_{PR}$) is shorter than the pacemaker-defined AV (or PV) interval. As discussed in more detail below, the occurrence of an R-wave is verified by a method of the present invention, i.e., the occurrence a number of consecutive R-waves (e.g. a programmable number, preferably greater than three) or, alternatively, the occurrence of an R-wave having the appropriate morphology.

The occurrence of a verified R-wave indicates the end of the conduction time $t_{AR}$ (or $t_{PR}$), and thus permits a measurement of $t_{AR}$ (or $t_{PR}$) to be completed (block 530), preferably based on a average of a at least three or a programmable number of naturally conducted R-waves. The measured value of $t_{AR}$ (or $t_{PR}$) is then used as a basis for decreasing the AV (or PV) interval (block 532). The AV interval is set to $t_{AR}$-X, where X is a parameter having a programmable value, a fixed value, or an adaptive value based on a percentage of the heart rate. Similarly, the PV interval is set to $t_{PR}$-Y, where Y is a parameter having a programmable value, a fixed value, or an adaptive value based on a percentage of the heart rate.

Alternatively, the AV (or PV) interval can be decreased by a programming interval Δ below the existing AV (or Pv) interval. Accordingly, the AV (or PV) interval is decreased by the programmable interval Δ without immediate measurement of the natural conduction time $t_{AR}$ or $t_{PR}$ (block 532').

In some embodiments of the invention, $t_{PR}$ and $t_{AR}$ are measured separately, and separate values are programmed or otherwise determined for the parameters X and Y. Thus, in such embodiments, $t_{PR}$ and the resulting PV interval, and $t_{AR}$ and the resulting AV interval, are totally independent of each other. In other embodiments, one of $t_{AR}$ or $t_{PR}$ is determined, e.g., whichever happens to occur first, and the other is computed as a function of the measured value. In such embodiments, $t_{AR}$ is set to be a prescribed number of ms greater than $t_{PR}$. In such embodiments, there is thus a prescribed relationship between $t_{AR}$ and $t_{PR}$ and the resulting AV and PV intervals. For most purposes relating to the description of the present invention, one of the AV (or PV) intervals, or one of the conduction times $t_{AR}$ (or $t_{PR}$), is all that is expressly referenced, and it is assumed that the other can be determined in an appropriate manner. Techniques for measuring the natural conduction time of a patient are described in U.S. Pat. No. 5,340,361, already incorporated herein by reference.

In another embodiment, the occurrence of ectopic R-waves that fall within a limited time window of, e.g., 50 ms, is highly unlikely. Thus, if an average conduction time $t_{AR}$ or ($t_{PR}$) for three consecutive R-waves is calculated, and the conduction time $t_{AR}$ or ($t_{PR}$) for each R-wave falls within plus or minus 25 ms of the calculated average conduction time, then the occurrence of a R-wave resulting from natural A-V conduction is considered to have been verified (block 506). Other similar techniques relating to the occurrence and timing of a series of R-wave likewise may be used to verify the occurrence of R-waves resulting from natural A-V conduction.

The assessment of the morphology of an R-wave (or QRS complex) requires the pacemaker to learn the morphology of an R-wave resulting from a native or natural ventricular depolarization. An R-wave's morphology is sampled by the sense and IEGM amplifiers 428 (FIG. 9) which samples the R-wave at a fixed sample rate of, e.g., 256 bytes per second. Thus, in the learn mode, a native R-wave is sampled and the resulting data bytes stored. In an operational mode, a measured R-wave is sampled and converted to data bytes. The data from the measured R-wave is compared with the stored data from the native R-wave and a correlation figure calculated. If the correlation figure exceeds a predetermined threshold, then the measured R-wave is considered a verified R-wave, and if appropriate, the pacemaker performs the necessary AV/PV interval adjustments. If the correlation figure fails to exceed the predetermined threshold, the measured R-wave is considered an ectopic R-wave and ignored.

In still another embodiment, an R-wave may be verified (block 528) by analyzing the timing or the morphology of the R-wave. To allow for changes in R-wave morphology over time, a physician also may have R-wave signals digitized and transmitted via a telemetry interface 110 (FIG. 6) to an external programmer 108 where the signals are converted back to their original analog form for display. If desired, the physician may "reset" the stored native morphology. More specifically, the physician, using external program control of the microprocessor control and timing circuit 86, temporarily increases the AV/PV interval to enable the occurrence of intact AV nodal conduction. A newly acquired R-wave is then transmitted to a display for the physician's approval. Upon approval, the new native morphology is stored as the reference R-wave morphology. It is further possible to have multiple morphologies stored in memory, with a particular morphology being selected by the physician or automatically being selected based on the patient's physiological condition. Another representative morphology system for use in implementing the pacemaker of the present invention is described in U.S. Pat. No. 5,513,644, incorporated herein by reference.

Thus, it is seen that the present invention provides an implantable pacemaker, and method of operating such a pacemaker, that can set the AV (or PV) interval of the pacemaker to a value that is derived from the measured natural conduction time of the patient. For treating HOCM, for example, such pacemaker and method stimulates the cardiac tissue at a time in the cardiac cycle that is just prior to when natural depolarization of the cardiac tissue would otherwise cause a cardiac contraction, and in so doing, creates a mechanical contraction sequence that, for most patients, improves the cardiac output.

As further described above, it is seen that the invention provides a dual-chamber pacemaker, and method of operating such a dual-chamber pacemaker, that automatically sets and adjusts the pacemaker-defined AV (or PV) interval to a value that is generally just less than the natural conduction time of the patient. Such action advantageously causes a V-pulse to be generated and delivered to the ventricular muscle tissue at a time in the cardiac cycle that suits a particular purpose (e.g., treating a HOCM or providing demand pacing), while still maintaining the approximate cardiac timing set by the natural conduction time.

As also described above, and for use with HOCM treatment, it is seen that the invention provides a dual-chamber pacemaker, and method of operating such a pacemaker, that decreases the pacemaker-defined AV interval in response to sensing a verified R-wave (which verified R-wave evidences a shortened natural conduction time), and that automatically increases the pacemaker-defined AV interval in prescribed increments in response to not sensing an R-wave for a prescribed number of consecutive cardiac cycles (which failure to sense any R-waves may evidence a lengthening of the natural conduction time). Thus, advantageously, the pacemaker-defined AV interval is most always set to a value that is just somewhat less than the natural conduction time, regardless of whether the natural conduction time is increasing or decreasing, and the cardiac output of the patient is maximized.

While the invention herein disclosed has been described by means of specific embodiments and applications thereof, numerous modifications and variations could be made thereto by those skilled in the art without departing from the scope of the invention set forth in the claims.

What is claimed is:

1. A dual-chamber programmable pacemaker for enhancing cardiac performance of a patient suffering from hypertrophic obstructive cardiomyopathy, comprising:
    sensing means for sensing P-waves and R-waves, associated with natural atrial and ventricular contractions, respectively;
    means for storing a morphology signal for a naturally-conducted selected reference R-wave resulting from a natural ventricular depolarization;
    means for comparing the reference R-wave and a current R-wave and for verifying, based on such comparison, whether the current R-wave has the morphology of a naturally-conducted R-wave or is the result of an ectopic R-wave;
    processing means for adjusting an AV/PV interval in accordance with a predetermined strategy when it is verified that a current R-wave has the morphology of a selected reference R-wave and wherein the current R-wave is considered an ectopic R-wave when the current R-wave does not have the morphology of a selected reference R-wave.

2. A dual-chamber programmable pacemaker, as defined in claim 1, wherein the comparing means includes means for calculating a correlation figure based upon the correlation of the stored selected reference R-wave morphology with a current R-wave, and wherein when the correlation figure exceeds a predetermined threshold, the current R-wave is considered a verified R-wave, and wherein when the correlation figure fails to exceed the predetermined threshold, the current R-wave is considered an ectopic R-wave.

3. The dual-chamber programmable pacemaker, as defined in claim 1, further comprising means for resetting the stored selected reference R-wave morphology to a new morphology.

4. The dual-chamber programmable pacemaker, as defined in claim 3, wherein the resetting means comprises means for telemetrically communicating with an external programmer for resetting the stored reference R-wave morphology to the new morphology.

5. The dual-chamber programmable pacemaker, as defined in claim 1, wherein the storing means includes means for storing a plurality of selected R-wave morphologies, and wherein each one of the plurality of such morphologies is selectable based upon a patient's physiological condition.

6. The dual-chamber programmable pacemaker, as defined in claim 1, further comprising:
    means for determining a natural conduction time interval between an atrial event, either a P-wave or a paced atrial event, and a verified naturally-conducted R-wave; and
    wherein the processing means adjusts the AV/PV interval between the atrial event and a paced ventricular contraction to a value that is a prescribed time interval less than the natural conduction time interval.

7. The dual-chamber programmable pacemaker, as defined in claim 6, wherein the processing means, after shortening the AV/PV interval, returns the AV/PV interval to its initial value after a predetermined number of paced ventricular contractions.

8. The dual-chamber programmable pacemaker, as defined in claim 7, wherein the prescribed time interval is 5–100 ms and the predetermined number of paced ventricular contractions is between 4 and 512.

9. A method of operating a dual-chamber programmable pacemaker for enhancing cardiac performance of a patient suffering from hypertrophic obstructive cardiomyopathy, comprising the steps of:
    sensing an R-wave;
    storing morphology signals for a naturally-conducted selected reference R-wave;
    comparing the morphology of a current sensed R-wave with the morphology of a stored reference R-wave to verify that the sensed R-wave has the morphology of a conducted ventricular contraction and is not the result of an ectopic ventricular contraction;
    setting an AV/PV interval in accordance with a predetermined strategy when a sensed R-wave is verified as resulting from a conducted ventricular contraction.

10. The method of operating a dual-chamber programmable pacemaker, as defined in claim 9, the comparing step further comprising the step of:
    calculating a correlation figure based upon the correlation of the morphology of the stored selected reference R-wave with the morphology of a current R-wave; and
    determining if the correlation figure exceeds a predetermined threshold to indicate a verified R-wave, and if the correlation figure fails to exceed the predetermined threshold to indicate that the current R-wave is an ectopic R-wave.

11. The method of operating a dual-chamber programmable pacemaker, as defined in claim 9, further comprising the step of:
    storing a plurality of R-wave morphologies; and
    selecting the reference R-wave from the plurality of R-wave morphologies stored in the processor.

12. The method of operating a dual-chamber programmable pacemaker, as defined in claim 11, further comprising the steps of:
    generating physiological signal representing the patient's physiological condition; and
    automatically selecting the reference R-wave based on the patient's physiological condition.

13. The method of operating a dual-chamber programmable pacemaker, as defined in claim 9, further comprising the step of:
    resetting the stored reference R-wave to a new morphology.

14. The method of operating a dual-chamber programmable pacemaker, as defined in claim 9, further comprising the steps of:
    measuring the conduction time interval based upon an atrial event and a verified R-wave; and
    setting an AV/PV interval between an atrial event and a paced ventricular contraction to a value that is a prescribed time interval less than the measured conduction time interval.

15. The method of operating a dual-chamber programmable pacemaker, as defined in claim 14, further comprising the step of:
    decreasing the value of the AV/PV interval by a first predetermined time interval in response to at least three consecutive verified R-waves indicative of natural ventricular contractions.

* * * * *